United States Patent [19]
Ceprini et al.

[11] 3,932,285
[45] Jan. 13, 1976

[54] CHROMIUM SALT COMPOSITIONS AND A PROCESS FOR THEIR PRODUCTION

[75] Inventors: Mario Q. Ceprini, Cedarhurst, N.Y.; Roy T. Gottesman, Glen Rock, N.J.

[73] Assignee: Tenneco Chemicals, Inc., Saddle Brook, N.J.

[22] Filed: Oct. 3, 1973

[21] Appl. No.: 403,319

[52] U.S. Cl. ................... 252/1; 8/29; 252/389 R; 252/431 C; 252/467; 260/438.5 R; 260/687
[51] Int. Cl.² ........................................... C09K 3/00
[58] Field of Search ....... 252/1, 431 C; 260/438.5 R

[56] References Cited
UNITED STATES PATENTS
3,136,796   6/1964   Trebilcock ........................ 252/1 X

*Primary Examiner*—Leland A. Sebastian
*Assistant Examiner*—E. Suzanne Parr
*Attorney, Agent, or Firm*—Evelyn Berlow

[57] ABSTRACT

Stable solutions that contain at least 7.5% by weight of dissolved chromium comprise an organic solvent and a mixture of chromium salts that contains at least one chromium salt of a straight-chain aliphatic monocarboxylic acid having 5 to 10 carbon atoms and at least one chromium salt of a branched-chain aliphatic monocarboxylic acid having 5 to 10 carbon atoms.

32 Claims, No Drawings

CHROMIUM SALT COMPOSITIONS AND A PROCESS FOR THEIR PRODUCTION

This invention relates to organic solvent-soluble chromium salt compositions and to solutions of these compositions that contain at least 7.5% by weight of dissolved chromium. It further relates to a process for the preparation of these solutions.

Chromium salts of aliphatic monocarboxylic acids have found widespread use in industry. They are used, for example, in the preparation of paints and varnishes, as dewaxing agents, as catalysts in such chemical processes as the synthesis of polyolefins and the oxidation of cyclohexane to compounds useful as intermediates in the production of nylon, as complexers in the dyeing of certain types of fibers, and as corrosion inhibitors in fuels for gas turbine engines. In these and other applications, it is preferred that the chromium salts be dissolved in organic solvents to form stable solutions that have relatively low viscosities even at relatively high metal salt concentrations.

A number of processes for the preparation of chromium salts of organic acids have been described in the literature, but none teaches the preparation of stable compositions of high chromium content that have relatively low viscosities. For example, Malik and Ahmad in J. Amer. Oil Chem. Soc., 42, 451–6 (1965) described the preparation of chromium salts of stearic acid and palmitic acid by direct methathesis from the corresponding sodium soaps and chrome alum. The resulting soaps, which contained less than 6.5% Cr, were dissolved in hot organic solvents to form solutions from which, on cooling, the chromium salts separated as sticky amorphous masses which became glossy solids on ageing. In U.S. Pat. No. 3,558,676, Doherty disclosed a process in which metallic salts of fatty acids were reacted with basic chromic sulfate to form fatty acid chromic sulfate complexes, which were coordination compounds of the Werner type.

This invention is directed to stable chromium salt solutions that contain at least 7.5% by weight and in most cases at least 8.0% by weight of dissolved chromium and that have relatively low viscosities.

These chromium salt solutions comprise an organic solvent and a mixture of chromium salts of aliphatic monocarboxylic acids having 5 to 10 carbon atoms that includes one or more salts of straight-chain acids and one or more salts of branched-chain acids. The mixtures of chromium salts that form solutions having the desired combination of properties contain from about 20 to 80 mole percent of at least one chromium salt of a straight-chain acid and 20 to 80 mole percent of at least one chromium salt of a branched-chain acid. Mixtures that contain 40 to 60 mole percent of a salt of a straight-chain acid and 40 to 60 mole percent of a salt of a branched-chain acid are generally preferred. Solutions that have a particularly advantageous combination of properties result when the mixture of chromium salts contains substantially equimolar amounts of salts of straight-chain and branched-chain acids.

The chromium salt compositions of this invention may be prepared by any suitable and convenient procedure. For example, they may be prepared by forming a mixture of chromium salts and dissolving this mixture of salts in an organic solvent, by dissolving the individual salts in an organic solvent, by dissolving one of the salts in a solution containing the other salt, or by mixing a solution of one of the salts with a solution of the other salt.

In a preferred process for the preparation of the chromium salt compositions of this invention, a mixture of water-soluble salts of straight-chain and branched-chain aliphatic monocarboxylic acids having 5 to 10 carbon atoms is reacted with a water-soluble chromic salt of an inorganic acid in aqueous solution in the presence of a water-insoluble organic solvent. The chromium salts of the aliphatic acids, which are formed almost immediately, dissolve in the organic solvent, while the by-product salts remain in aqueous solution. The solution of chromium salts, which can be readily separated from the aqueous solution, contains at least 7.5% by weight of dissolved chromium and has a relatively low viscosity.

This solution can be washed with water to remove the small amounts of by-product salts that are present, or it can be used without further treatment or purification as a source of soluble chromium. Alternatively, it can be heated under vacuum to remove the solvent and thereby form a dry mixture of organic solvent-soluble chromium salts.

The straight-chain acids that can be used in the preparation of the chromium salt compositions of this invention are the saturated and unsaturated aliphatic monocarboxylic acids that have from 5 to 10 carbon atoms. They include n-pentanoic acid, n-hexanoic acid, n-heptanoic acid, n-octanoic acid, n-nonanoic acid, n-decanoic acid, 4-pentenoic acid, 3-hexenoic acid, and the like. The preferred straight-chain acid is n-hexanoic acid.

The branched-chain acids that can be used in the preparation of the chromium salt compositions are the saturated and unsaturated aliphatic monocarboxylic acids that have 5 to 10 carbon atoms and that have branching at one or more of the alpha and beta positions of the carbon chain. Illustrative of these alpha-branched-chain acids are 2-methylbutanoic acid, 2-ethylbutanoic acid, 2,2-dimethylbutanoic acid, 2-methyl-2-isopropylbutanoic acid, 2-methylheptanoic acid, 2-ethylhexanoic acid, 2-methylnonanoic acid, 2,2-dimethyloctanoic acid, 2-propylheptanoic acid, 2-ethyl-2-hexenoic acid, 2-propyl-4-pentenoic acid, and the like. The beta-branched-chain acids that can be used include 3-methylbutanoic acid, 3,3-dimethylbutanoic acid, 3-ethylpentanoic acid, 3-propylheptanoic acid, 3,3-dimethyloctanoic acid, 3-methyl-3-ethylheptanoic acid, 3-methyl-3-hexenoic acid, 3-isopropyl-2-hexenoic acid, and 3-ethyl-2-heptenoic acid. Compounds that have branching at both the alpha-position and the beta-position can also be used. Examples of these acids are 2,3-dimethylbutanoic acid, 2,3-dimethylpentanoic acid, 2-ethyl-3-methylbutanoic acid, 2-methyl-3,3-diethylpentanoic acid, 2-methyl-3-ethylheptanoic acid, 2-propyl-3-methylhexanoic acid, 2,2,3,3-tetramethylhexanoic acid, 2,3-dimethyl-3-hexenoic acid, and 2-ethyl-3-propylacrylic acid. Acids that have branching at the gamma or delta position as well as at the alpha and/or beta position and that can be used in the preparation of the chromium salts include 2-ethyl-4-methylpentanoic acid, 2-ethyl-5,5-dimethylhexanoic acid, 3,5,5-trimethylhexanoic acid, 2,2,4,4-tetramethylpentanoic acid, 2-methyl-5-ethylheptanoic acid, 2-propyl-5-methylhexanoic acid, 3-ethyl-4-methylpentanoic acid, 2-methyl-4,5-diethylbutanoic acid, 2,4-dimethyl-2-hexenoic acid, and 2,4,5-trimethyl-3-hexenoic acid.

The water-soluble salts of the aliphatic acids that can be used in this process include the alkali metal salts, that is, the sodium, potassium, and lithium salts, and the ammonium salts. The ammonium and sodium salts are preferred.

The water-soluble chromium compounds that are reacted with the salts of the aliphatic acids are chromic salts of inorganic acids, such as chromic chloride, chromic bromide, chromic nitrate, and chromic sulfate. Chromic chloride is generally preferred.

The solvents that are used in the process are inert, water-insoluble organic solvents including hydrocarbons, chlorinated hydrocarbons, alkanols having 4 to 10 carbon atoms, heterocyclic compounds, and mixtures thereof. The hydrocarbons that can be used include mineral spirits, kerosene, naphtha, n-hexane, n-heptane, n-octane, cyclohexane, cycloheptane, benzene, toluene, xylene, dipentene, turpentine, and other commonly-available economical hydrocarbons having low toxicity and odor. Other useful solvents are chloroform, carbon tetrachloride, dichloroethylene, chlorobenzene, chlorotoluene, isobutanol, n-amyl alcohol, iso-octanol, n-decanol, pyridine, and piperidine. For most applications, the preferred solvents are mixtures of hydrocarbons that are obtained by the fractional distillation of petroleum and that have from about 8 to 20 carbon atoms. Illustrative of these preferred solvents are the following:

|  | Boiling Range (°C.) |
|---|---|
| Gasoline | 70–200 |
| Kerosene | 90–315 |
| Mineral spirits | 160–190 |
| Jet Fuel | 210–290 |
| Mineral seal oil | 260–330 |

The amount of solvent used is that which will provide a chromium salt solution having the desired content of dissolved chromium and viscosity.

The temperature at which the reaction is carried out is not critical and may be between 40°C. and 100°C. When sodium salts of the aliphatic acids are used in the reaction, the preferred temperature range is 90° to 95°C.; when the ammonium salts are used, the preferred temperature range is 50° to 55°C.

In a preferred embodiment of the invention, chromium salt solutions that contain less than 0.02% by weight of sodium and potassium ions are prepared by reacting the ammonium salts of a mixture of straight-chain and branched-chain aliphatic monocarboxylic acids with chromic chloride hexahydrate in aqueous solution in the presence of a hydrocarbon solvent, such as mineral spirits, mineral seal oil,kerosene, jet fuel, or cyclohexane. Because they are substantially free of sodium and potassium ions, the compositions prepared in this way can be used as the corrosion inhibitor in fuels for gas turbine engines.

In addition to forming alkali metal-free compositions, the process in which the ammonium salts of the aliphatic acids are used is simpler and more efficient than that in which the sodium salts are used. When the chromium salts are formed by the reaction of chromic chloride with the sodium salts of the aliphatic acids, the resulting organic phase must be washed with large volumes of water to remove by-product sodium chloride from it and then dried and concentrated to bring its chromium content to the desired level. During these steps, the organic phase frequently thickens and becomes gel-like. When this thickening occurs, extended heating is necessary to release the trapped water and thereby reduce the viscosity of the composition. In addition, emulsification of the organic phase may occur during the washing step. This interferes with the removal of sodium chloride and also makes it necessary to heat the composition for long periods of time to insure the complete removal of water from it. When ammonium salts of the aliphatic acids are used in the process, a very fluid ungelled organic phase is obtained that requires little or no washing and that is readily dried. Since the reaction involving the ammonium salts takes place at a lower temperature than that involving the sodium salts (50°–55°C. vs. 90°–95°C.), processing time is substantially reduced, which results in a more efficient and economical commercial operation.

The chromium salt solutions of this invention contain at least 7.5% by weight and preferably 8.0 to 10% by weight of dissolved chromium as the metal; the actual metal content is limited for a particular salt composition by the molecular weights of the acids used in its preparation and the viscosity desired for the chromium salt solution. If desired, peptizing agents, such as dipropylene glycol and tripropylene glycol, can be used to decrease the viscosity of the solution.

The invention is further illustrated by the following examples. In these examples, viscosity was determined in accordance with the Gardner-Holdt procedure using a bubble viscosimeter. This method is fully described in various texts including "Stewart's Scientific Dictionary," 4th Edition, published by Stewart Research Laboratory, Alexandria, Va.

EXAMPLE 1

A mixture of 822 grams of water, 48 grams (1.2 moles) of sodium hydroxide, 87 grams (0.6 mole) of 2-ethylhexanoic acid, 70.2 grams (0.6 mole) of n-hexanoic acid, and 300 grams of mineral spirits (boiling range, 160°–190°C.) was vigorously agitated and heated to 93°–95°C. To this mixture was added 153.3 grams (0.36 mole) of chromic chloride hexahydrate as a 62% aqueous solution over a period of about 15 minutes. Agitation was continued at 93°–95°C. for 15 minutes. When the agitation was stopped, the reaction mixture separated into two phases. The lower aqueous phase was discarded. The organic phase was washed with 1050 ml. of water at 55°–60°C. and then heated at 130°C./25 mm Hg for 2 hours to distill off all of the water and mineral spirits. There was obtained 154.6 grams of a residue that contained equimolar amounts of chromium n-hexanoate and chromium 2-ethylhexanoate.

When the residue had cooled to 70°C., 114 grams of cyclohexane and 3 grams of filter aid (Celite 503) were added to it. The mixture was filtered at 70°C. through a filter that had been precoated with 9 grams of filter aid. The filter cake was washed with cyclohexane. The filtrate and the cyclohexane used to wash the filter cake were combined and concentrated by distillation until 234 grams of solution remained.

This solution, which contained equimolar amounts of chromium n-hexanoate and chromium 2-ethylhexanoate dissolved in cyclohexane, contained 8.02% Cr (100% recovery) and had a Gardner-Holdt viscosity at 25°C. of J.

COMPARATIVE EXAMPLE A

A mixture of 274 grams of water, 14.4 grams (0.36 mole) of sodium hydroxide, 54.4 grams (0.38 mole) of 2-ethylhexanoic acid, and 155 grams of cyclohexane was agitated and heated to its reflux temperature (71°C.). To this mixture was added 230.2 grams (0.54 mole) of a 62% aqueous solution of chromic chloride hexahydrate. Agitation was continued at 70°C. for 15 minutes. When the agitation was stopped, the reaction mixture separated into two phases. The lower aqueous phase was discarded. The organic phase was washed with two 250 ml. portions of water at 50°C. and dried. Then 185 grams of cyclohexane was added to the residue. The resulting very viscous solution of chromium 2-ethylhexanoate in cyclohexane contained 3.1% Cr.

COMPARATIVE EXAMPLE B

The procedure described in Comparative Example A was repeated using 155 grams of toluene in place of the cyclohexane. The product obtained, which was very viscous, contained 5.0% Cr.

COMPARATIVE EXAMPLE C

The procedure described in Comparative Example A was repeated using 46.9 grams (0.4 mole) of n-hexanoic acid in place of the 2-ethylhexanoic acid. The product, which contained 8% Cr, was very viscous and could not be poured at ambient temperature.

EXAMPLE 2

A mixture of 2700 grams of water, 773 grams (4.8 moles) of a 24.8% aqueous sodium hydroxide solution, 352 grams (2.44 moles) of 2-ethylhexanoic acid, 280.8 grams (2.37 moles) of n-hexanoic acid, and 1200 grams of mineral spirits was vigorously agitated and heated to 93°–95°C. To this mixture was added 613.2 grams (1.44 moles) of a 62% aqueous solution of chromic chloride hexahydrate over a period of 15 minutes. Agitation was continued at 93°–95°C. for 15 minutes. When the agitation was stopped, the reaction mixture separated into two phases. The lower aqueous phase was discarded. The organic phase was washed with 4000 ml water at 55°–60°C. The resulting gelatinous organic phase was heated to 125°C./115 mm Hg. During this heating period, the organic phase of a duplicate batch was fed continuously into the distilling flask, while mineral spirits and water were distilled from it. During the distillation, there was a dramatic reduction in the viscosity of the reaction mixture and its color changed from blue-violet to emerald green. The distillation was continued until a residue of 1542 grams remained. This residue consisted of chromium n-hexanoate and chromium 2-ethylhexanoate. When the residue had cooled to 100°C., 158 grams of mineral spirits and 12 grams of filter aid (Celite 503) were added to it, and the resulting slurry was filtered at 100°C. through a filter that had been precoated with filter aid. The filter cake was washed with mineral spirits. The mineral spirits used to wash the filter cake and additional mineral spirits were added to the filtrate to bring its weight to 1841 grams.

The resulting solution of chromium n-hexanoate and chromium 2-ethylhexanoate in mineral spirits contained 8.04% Cr (99.5% recovery); had a Gardner-Holdt viscosity at 25°C. of E, and contained 0.02% of sodium.

EXAMPLE 3

A mixture of 1500 grams of water, 730 grams of a 26.2% aqueous sodium hydroxide solution, 352 grams (2.44 moles) of 2-ethylhexanoic acid, 280.8 grams (2.37 moles) of n-hexanoic acid, and 1000 grams of mineral seal oil (boiling range, 260°–330°C.) was agitated and heated to 93°–95°C. To this mixture was added 613.2 grams (1.44 moles) of a 62% aqueous solution of chromic chloride hexahydrate over a period of 15 minutes. Agitation was continued for 15 minutes. When the agitation was stopped, the reaction mixture separated into two phases. The aqueous phase was discarded. The gelatinous organic phase was washed with four 2000 ml. portions of water at 55°–60°C. and then heated to 130°C./125 mm Hg. During the distillation, the viscosity of the mixture was gradually reduced, and its color changed from blue to green. The distillation was continued until a residue of 715 grams remained. This residue at 110°C. was filtered through a filter that had been precoated with filter aid (Celite 503) and then diluted with 205 grams of mineral seal oil. The resulting solution, which contained 8.0% Cr, had a Gardner-Holdt viscosity at 25°C. of L.

EXAMPLE 4

The procedure described in Example 3 was repeated except that the solvent was jet fuel. This solvent, which is available as JP-5 Jet Fuel, has a flash point of 50°C. and a boiling range of 210°–290°C. The product obtained contained 8.06% Cr and had a Gardner-Holdt viscosity at 25°C. of H and a flash point of 55°C.

EXAMPLE 5

A mixture of 300 grams of water, 116.7 grams (1.96 moles) of a 28.6% aqueous ammonium hydroxide solution, 140.8 grams (0.98 mole) of 2-ethylhexanoic acid, 112.2 grams (0.948 mole) of n-hexanoic acid, and 118 grams of mineral seal oil was brought to 50°–51°C. To this mixture was added 257.5 grams (0.594 mole) of a 62% aqueous solution of chromic chloride hexahydrate over a period of 6 minutes while the reaction mixture was vigorously agitated. Then 10 ml. of water and 7.6 grams of a 28.6% aqueous ammonium hydroxide solution were added. Agitation was continued at 55°C. for 10 minutes and then stopped to allow the phases to separate. The lower aqueous phase was discarded. The organic phase was heated at 130°C./125 mm Hg for 1.5 hours. To the residue was added 3.7 grams of filter aid (Celite 503). The resulting slurry was filtered at 60°C.

There was obtained 370.7 grams of a solution that contained chromium n-hexanoate and chromium 2-ethylhexanoate that contained 8.07% Cr (96.6% recovery), and that had a Gardner-Holdt viscosity at 25°C. of R.

COMPARATIVE EXAMPLE D

The procedure described in Example 5 was repeated using 1.96 moles of n-hexanoic acid in place of the mixture of acids. There was obtained 362.3 grams of a solution of chromium n-hexanoate in mineral seal oil that contained about 8% Cr and that had a very high viscosity. On standing overnight, the product separated into two phases.

COMPARATIVE EXAMPLE E

The procedure described in Example 5 was repeated using 278 grams (1.92 moles) of 2-ethylhexanoic acid in place of the mixture of acids. There was obtained 380.6 grams of a very viscous solution of chromium 2-ethylhexanoate in mineral seal oil that contained 6.8% Cr.

EXAMPLE 6

To a mixture of 2400 grams of water, 1689.6 grams (11.7 moles) of 2-ethylhexanoic acid, 1346.4 grams (11.35 moles) of n-hexanoic acid, and 1400 grams (23.5 moles) of a 28.6% aqueous ammonium hydroxide solution at 64°C. was added 1415 grams of kerosene. The mixture was cooled to 50°C., and it was vigorously agitated while 3090 grams (7.13 moles) of a 62% aqueous solution of chromic chloride hexahydrate was added to it over a period of 6 minutes. An additional 120 grams of water and 182.8 grams (0.306 mole) of the 28.6% ammonium hydroxide solution were added. Agitation was continued at 50°C. for 10 minutes, and the phases were then allowed to separate. The aqueous phase was discarded. The organic phase was heated at 130°C./125 mm Hg for 1.5 hours. To the residue were added 45.0 grams of filter aid (Celite 512) and 186 grams of kerosene. The resulting slurry was cooled to 60°C. and filtered.

There was obtained 4429.7 grams of a chromium mixed salt solution that contained 8.08% Cr (96.4% recovery) and had a Gardner-Holdt viscosity at 25°C. of M.

EXAMPLE 7

To a mixture of 1000 grams of water, 704.6 grams of 2-ethylhexanoic acid, and 561.4 grams of n-hexanoic acid was added 583.8 grams of a 28.6% aqueous solution of ammonium hydroxide. The temperature of the reaction mixture rose to 65°C. To this mixture was added 590 grams of kerosene. The mixture was cooled to 50°C., and 1288.5 grams of a 62% aqueous solution of chromic chloride hexahydrate was added to it. After the addition of 50 grams of water and 38.1 grams of the ammonium hydroxide solution, the mixture was agitated for 10 minutes and then allowed to separate into phases. The aqueous phase was discarded. The organic phase was heated to 130°C./125 mm Hg. To the residue were added 19 grams of filter aid (Celite 512) and 75 grams of kerosene. The resulting slurry was cooled to 60°C. and filtered.

There was obtained 1843.6 grams of a chromium mixed salt solution that contained 8.1% Cr (96.7% recovery) and had a Gardner-Holdt viscosity at 25°C. of L.

EXAMPLE 8

To a mixture of 400 grams of water, 443.5 grams (3.07 moles) of 2-ethylhexanoic acid, and 90.8 grams (0.767 mole) of n-hexanoic acid, was added 233 grams (3.91 moles) of a 28.6% aqueous ammonium hydroxide solution. The temperature of the reaction mixture rose to 63°C. To this mixture was added 207 grams of mineral seal oil. The mixture was cooled to 50°C., and 515 grams (1.189 moles) of a 62% aqueous solution of chromic chloride hexahydrate was added to it. After the addition of 20 grams of water and 15.2 grams of the ammonium hydroxide solution, the mixture was agitated for 10 minutes and then allowed to separate into phases. The aqueous phase was discarded. The organic phase was dried at 130°C./125 mm Hg for 1.5 hours and then cooled to 60°C. Filter aid (Celite 512) was added, and the slurry was filtered.

There was obtained 777 grams of a chromium mixed salt solution that contained 8.14% Cr (100% recovery) and had a Gardner-Holdt viscosity at 25°C. of S.

EXAMPLE 9

The procedure described in Example 8 was repeated except that 111.1 grams (0.767 mole) of 2-ethylhexanoic acid and 363 grams (3.07 moles) of n-hexanoic acid were used.

There was obtained 719.1 grams of a chromium mixed salt solution that contained 8.06% Cr and had a Gardner-Holdt viscosity at 25°C. of Z+.

EXAMPLE 10

The procedure described in Example 8 was repeated except that kerosene was used in place of mineral seal oil. At the end of the vacuum drying step, 18.3 grams of the 24.4 grams of kerosene that had codistilled during drying was added to the product prior to filtration. There was obtained 768.8 grams of a chromium mixed salt solution that contained 7.9% Cr (98.3% recovery) and had a Gardner-Holdt viscosity at 25°C. of K.

EXAMPLE 11

The procedure described in Example 8 was repeated except that 281.6 grams (1.95 moles) of 2-ethyl-4-methylpentanoic acid and 224.4 grams (1.89 moles) of n-hexanoic acid were used as the acid mixture.

There was obtained 768.4 grams of a chromium mixed salt solution that contained 8.2% Cr (100% recovery). When this solution was diluted with 15 grams of mineral seal oil, it contained 8.0% Cr and had a Gardner-Holdt viscosity at 25°C. of S.

COMPARATIVE EXAMPLE F

The procedure described in Example 8 was repeated except that 563.2 grams of 2-ethyl-4-methylpentanoic acid was used in place of the mixture of acids.

The product obtained was very viscous and could not be filtered.

COMPARATIVE EXAMPLE G

The procedure described in Example 8 was repeated except that 113.5 grams of 4-methylpentanoic acid was used in place of the 2-ethylhexanoic acid.

The very viscous product obtained was unstable and separated into two phases on standing.

EXAMPLE 12

To a mixture of 120 grams of water, 115.9 grams (0.67 mole) of 2-propylheptanoic acid and 78 grams (0.66 mole) of n-hexanoic acid was added 81.5 grams (1.37 moles) of a 28.6% aqueous ammonium hydroxide solution. The temperature of the reaction mixture rose to 60°C. To this mixture was added 82.2 grams of mineral seal oil. The mixture was cooled to 50°C., and 180.2 grams of a 62% aqueous solution of chromic chloride hexahydrate was added to it. After the addition of 7 grams of water and 5.3 grams of the ammonium hydroxide solution, the mixture was agitated for 10 minutes and then allowed to separate into phases. The aqueous phase was discarded. The organic phase was dried at 130°C./125 mm Hg for 1.5 hours and then cooled to 60°C. and filtered. There was obtained 282.7 grams of a chromium mixed salt solution that contained 7.5% Cr (98.1 % recovery) and had a Gardner-Holdt viscosity at 25°C. of S.

EXAMPLE 13

The procedure described in Example 8 was repeated except that the acid mixture was replaced by 310 grams (1.96 moles) of 3,5,5-trimethylhexanoic acid and 224.4 grams (1.89 moles) of n-hexanoic acid.

There was obtained 765 grams of a chromium mixed salt solution that contained 7.7% Cr (95.7% recovery) and had a Gardner-Holdt viscosity at 25°C. of Z–2.

COMPARATIVE EXAMPLE H

The procedure described in Example 8 was repeated except that 620 grams of 3,5,5-trimethylhexanoic acid was used in place of the mixture of acids.

The product obtained, which was extremely viscous, separated into two phases on standing at ambient temperature.

EXAMPLE 14

The procedure described in Example 8 was repeated except that the acid mixture was replaced by 218 grams (1.95 moles) of 2-ethyl-3-propylacrylic acid and 224.4 grams (1.89 moles) of n-hexanoic acid.

There was obtained 765 grams of a chromium mixed salt solution that contained 7.7% Cr (91.6% recovery) and had a Gardner-Holdt viscosity at 25°C. of Y.

COMPARATIVE EXAMPLE I

The procedure described in Example 8 was repeated except that 562 grams of 2-ethyl-3-propylacrylic acid was used in place of the mixture of acids.

The product obtained contained 7.3% and had a Gardner-Holdt viscosity at 25°C. of X.

From the data in Examples 1–14 and Comparative Examples A-I, it will be seen that when a mixture of a straight-chain monocarboxylic acid and a monocarboxylic acid having branching at the alpha position and/or at the beta position is used in their preparation the chromium salts form stable solutions that contain at least 7.5% and in most cases at least 8.0% of dissolved chromium and that have relatively low viscosities. When a straight-chain acid or an alpha- or beta-branched-chain acid is used alone or in combination with a gamma-branched acid, the resulting chromium salts are less soluble in organic solvents and form solutions that contain less than 7.5% Cr, that are very viscous, and that are often unstable on standing.

What is claimed is:

1. A stable solution containing at least 7.5% by weight of dissolved chromium that comprises an inert, water-insoluble organic solvent and a mixture of chromium salts that contains 20 to 80 mole percent of at least one chromium (III) salt of a straight-chain aliphatic monocarboxylic acid having 5 to 10 carbon atoms and 20 to 80 mole percent of at least one chromium (III) salt of a branched-chain aliphatic monocarboxylic acid having 5 to 10 carbon atoms, said branched-chain acid having branching at one or more of the alpha and beta positions of the chain.

2. A stable solution as set forth in claim 1 that contains at least 8.0% by weight of dissolved chromium.

3. A stable solution as set forth in claim 1 wherein the mixture of chromium salts contains 40 to 60 mole percent of said chromium (III) salt of a straight-chain acid and 40 to 60 mole percent of said chromium (III) salt of a branched-chain acid.

4. A stable solution as set forth in claim 1 wherein the mixture of chromium salts contains about 50 mole percent of said chromium (III) salt of a straight-chain acid and 50 mole percent of said chromium (III) salt of a branched-chain acid.

5. A stable solution as set forth in claim 1 wherein the mixture of chromium (III) salts contains chromium 2-ethylhexanoate.

6. A stable solution as set forth in claim 1 wherein the mixture of chromium (III) salts contains chromium 2-ethyl-4-methylpentanoate.

7. A stable solution as set forth in claim 1 wherein the mixture of chromium (III) salts contains chromium 2-propylheptanoate.

8. A stable solution as set forth in claim 1 wherein the mixture of chromium (III) salts contains chromium 3,5,5-trimethylhexanoate.

9. A stable solution as set forth in claim 1 wherein the mixture of chromium (III) salts contains chromium 2-ethyl-3-propylacrylate.

10. A stable solution as set forth in claim 1 wherein the mixture of chromium (III) salts contains chromium n-hexanoate.

11. A stable solution as set forth in claim 1 wherein the organic solvent is an inert, water-insoluble organic solvent selected from the group consisting of hydrocarbons, chlorinated hydrocarbons, alkanols having 4 to 10 carbon atoms, heterocyclic compounds, and mixtures thereof.

12. A stable solution as set forth in claim 1 that comprises a mixture of about 50 mole percent of chromium (III) n-hexanoate and about 50 mole percent of chromium (III) 2-ethylhexanoate dissolved in a hydrocarbon solvent.

13. A chromium salt composition that comprises 20 to 80 mole percent of a chromium (III) salt of a straight-chain aliphatic monocarboxylic acid having 5 to 10 carbon atoms and 20 to 80 mole percent of a chromium (III) salt of a branched-chain aliphatic monocarboxylic acid having 5 to 10 carbon atoms, said branched-chain acid having branching in one or more of the alpha and beta positions of the chain.

14. A chromium salt compositon as set forth in claim 13 that comprises 40 to 60 mole percent of said chromium (III) salt of a straight-chain monocarboxylic acid and 40 to 60 mole percent of said chromium (III) salt of a branched-chain monocarboxylic acid.

15. A chromium salt composition as set forth in claim 13 that comprises about 50 mole percent of chromium (III) n-hexanoate and about 50 mole percent of chromium (III) 2-ethylhexanoate.

16. The process for the production of chromium salt compositions that contain at least 7.5% by weight of dissolved chromium that comprises the steps of
   a. contacting a mixture of water-soluble salts of aliphatic acids with a water-soluble chromic salt of an inorganic acid selected from the group consisting of chromic chloride, chromic bromide, chromic nitrate, and chromic sulfate in aqueous solution in the presence of an inert, water-insoluble organic solvent, said mixtures of water-soluble acid salts containing 20 to 80 mole percent of at least one water-soluble salt of a straight-chain aliphatic monocarboxylic acid having 5 to 10 carbon atoms and 20 to 80 mole percent of at least one water-soluble salt of a branched-chain aliphatic monocarboxylic acid having 5 to 10 carbon atoms, said branched-chain acid having branching at one or more of the alpha and beta positions of its chain; and b. recovering a chromium salt composition that is a solution of the chromium (III) salts of said aliphatic monocarboxylic acids in the organic solvent.

17. The process for the production of chromium salt compositions that contain at least 7.5% by weight of dissolved chromium that comprises the steps of
   a. contacting a mixture of ammonium salts of aliphatic acids with chromic chloride hexahydrate in aqueous solution in the presence of an inert water-insoluble organic solvent, said mixture of ammonium salts containing 20 to 80 mole percent of at least one salt of a straight-chain aliphatic monocarboxylic acid having 5 to 10 carbon atoms and 20 to 80 mole percent of at least one salt of a branched-chain aliphatic monocarboxylic acid having 5 to 10 carbon atoms, said branched-chain acid having branching at one or more of the alpha and beta positions of its chain; and
   b. recovering a chromium salt composition that is a solution of the chromium (III) salts of said aliphatic monocarboxylic acids in the organic solvent.

18. The process of claim 17 wherein the mixture of ammonium salts contains 40 to 60 mole percent of the salt of the straight-chain acid and 40 to 60 percent of the salt of the branched-chain acid.

19. The process of claim 17 wherein the mixture of ammonium salts contains about 50 mole percent of the salt of the straight-chain acid and about 50 mole percent of the salt of the branched-chain acid.

20. The process of claim 17 wherein the straight-chain acid is n-hexanoic acid.

21. The process of claim 17 wherein the branched-chain acid is 2-ethylhexanoic acid.

22. The process of claim 17 wherein the branched-chain acid is 2-ethyl-4-methylpentanoic acid.

23. The process of claim 17 wherein the branched-chain acid is 2-propylheptanoic acid.

24. The process of claim 17 wherein the branched-chain acid is 3,5,5-trimethylhexanoic acid.

25. The process of claim 17 wherein the branched-chain acid is 2-ethyl-3-propylacrylic acid.

26. The process of claim 17 wherein the mixture of ammonium salts is contacted with chromic chloride hexahydrate at a temperature in the range of 50° to 55°C.

27. The process of claim 17 wherein the organic solvent is selected from the group consisting of hydrocarbons, chlorinated hydrocarbons, alkanols having 4 to 10 carbon atoms, heterocyclic compounds, and mixtures thereof.

28. The process of claim 27 wherein the organic solvent is a hydrocarbon.

29. The process of claim 28 wherein the organic solvent is mineral seal oil.

30. The process of claim 28 wherein the organic solvent is mineral spirits.

31. The process of claim 28 wherein the organic solvent is kerosene.

32. The process of claim 17 wherein a mixture of chromium salts is recovered from said solution.

* * * * *